US010419862B2

(12) United States Patent
Santek

(10) Patent No.: US 10,419,862 B2
(45) Date of Patent: Sep. 17, 2019

(54) INCUS SHORT PROCESS ATTACHMENT FOR IMPLANTABLE FLOAT TRANSDUCER

(71) Applicant: MED-EL Elektromedizinische Geraete GmbH, Innsbruck (AT)

(72) Inventor: Michael Santek, Innsbruck (AT)

(73) Assignee: MED-EL Elektromedizinische Geraete GmbH, Innsbruck (AT)

( * ) Notice: Subject to any disclaimer, the term of this patent is extended or adjusted under 35 U.S.C. 154(b) by 221 days.

(21) Appl. No.: 15/517,547

(22) PCT Filed: Nov. 11, 2015

(86) PCT No.: PCT/US2015/060069
§ 371 (c)(1),
(2) Date: Apr. 7, 2017

(87) PCT Pub. No.: WO2016/077411
PCT Pub. Date: May 19, 2016

(65) Prior Publication Data
US 2017/0325034 A1 Nov. 9, 2017

Related U.S. Application Data

(60) Provisional application No. 62/078,541, filed on Nov. 12, 2014.

(51) Int. Cl.
*H04R 25/00* (2006.01)
*A61F 2/18* (2006.01)

(52) U.S. Cl.
CPC ............. *H04R 25/606* (2013.01); *A61F 2/18* (2013.01); *H04R 25/60* (2013.01); *A61F 2002/183* (2013.01)

(58) Field of Classification Search
CPC .... H04R 25/00–75; H04R 2225/00–83; H04R 2460/00–17
See application file for complete search history.

(56) References Cited

U.S. PATENT DOCUMENTS 6,537,199 B1 3/2003 Müller et al.
6,540,661 B1 4/2003 Müller
(Continued)

OTHER PUBLICATIONS

International Searching Authority, International Search Report—International Application No. PCT/US15/60069, dated Jan. 29, 2016, together with the Written Opinion of the International Searching Authority, 14 pages.

*Primary Examiner* — Thaddeus B Cox
(74) *Attorney, Agent, or Firm* — Sunstein Kann Murphy & Timbers LLP

(57) ABSTRACT

A middle ear prosthesis coupling member is described that includes a transducer coupling element adapted for coupling to a mechanical signal transducer, and an ossicle fastener coupled to the transducer coupling element and adapted for secure attachment to the short process of the incus ossicle of a patient middle ear. The ossicle fastener includes parallel separated first and second fastener clips. Each fastener clip has two opposing bendable legs adapted for forming an interior region for receiving the short process of the incus ossicle and a relieved opening between opposing leg ends displaceably providing access for the incus ossicle to the interior region. The fastener clips securely enclose the short process of the incus ossicle within the interior region. The first fastener clip is adapted for exerting a force to pull the ossicle fastener toward the short process of the incus ossicle. The second fastener clip is adapted for holding the ossicle fastener in place over lateral movement on the short process of the incus ossicle only and without substantially exerting a force to pull the ossicle fastener toward the short process of the incus ossicle.

17 Claims, 4 Drawing Sheets

(56) References Cited

U.S. PATENT DOCUMENTS

| | | |
|---|---|---|
| 6,726,719 B2 | 4/2004 | Antonelli et al. |
| 2009/0043149 A1* | 2/2009 | Abel .................... H04R 25/606 600/25 |
| 2012/0078368 A1* | 3/2012 | Lenarz ...................... A61F 2/18 623/10 |
| 2013/0018217 A1 | 1/2013 | Santek et al. |

* cited by examiner

INCUS SHORT PROCESS ATTACHMENT FOR IMPLANTABLE FLOAT TRANSDUCER

This application is a national phase entry of Patent Cooperation Treaty Application PCT/US2015/060069, filed Nov. 11, 2015, which in turn claims priority from U.S. Provisional Patent Application 62/078,541, filed Nov. 12, 2014, which is incorporated herein by reference in its entirety.

TECHNICAL FIELD

The present invention relates to medical implants and more specifically to a middle ear implant device and a middle ear prosthesis coupling member for fixating an implantable mechanical signal transducer to the short process of the incus ossicle in the middle ear of a patient.

BACKGROUND ART

A normal ear transmits sounds as shown in FIG. 1 through the outer ear 101 to the tympanic membrane (eardrum) 102, which moves the ossicles of the middle ear 103 (malleus, incus, and stapes) that vibrate the oval window and round window openings of the cochlea 104. The cochlea 104 is a long narrow organ wound spirally about its axis for approximately two and a half turns. It includes an upper channel known as the scala vestibuli and a lower channel known as the scala tympani, which are connected by the cochlear duct. The cochlea 104 forms an upright spiraling cone with a center called the modiolus where the spiral ganglion cells of the acoustic nerve 113 reside. In response to received sounds transmitted by the middle ear 103, the fluid-filled cochlea 104 functions as a transducer to generate electric pulses which are transmitted to the cochlear nerve 113, and ultimately to the brain.

Hearing is impaired when there are problems in the ear's ability to transduce external sounds into meaningful action potentials along the neural substrate of the cochlea 104. To improve impaired hearing, various types of hearing prostheses have been developed. For example, when a hearing impairment is related to the operation of the middle ear 103, a conventional hearing aid or a middle ear implant (MEI) device may be used to provide acoustic-mechanical vibration to the auditory system.

FIG. 1 also shows some components in a typical MEI arrangement where an external audio processor 111 processes ambient sounds to produce an implant communications signal that is transmitted through the skin to an implanted receiver 108. Receiver 108 includes a receiver coil that transcutaneously receives signals, the implant communications signal, which is then demodulated into a transducer stimulation signals which is sent over leads 109 through a surgically created channel in the temporal bone to a floating mass transducer (FMT) 110 secured to the incus bone in the middle ear 103. The transducer stimulation signals cause drive coils within the FMT 110 to generate varying magnetic fields which in turn vibrate a magnetic mass suspended within the FMT 110. The vibration of the inertial mass of the magnet within the FMT 110 creates vibration of the housing of the FMT 110 relative to the magnet. This vibration of the FMT 110 is coupled to the incus in the middle ear 103 and then to the cochlea 104 and is perceived by the user as sound. See U.S. Pat. No. 6,190,305, which is incorporated herein by reference.

Middle ear implants using electromagnetic transducers such as FMT 110 can present some problems. Many are installed using complex surgical procedures which present the usual risks associated with major surgery and which also require disarticulating (disconnecting) one or more of the bones of the middle ear 103. Disarticulation deprives the patient of any residual hearing he or she may have had prior to surgery, placing the patient in a worsened position if the implanted device is later found to be ineffective with improving the patient's hearing. Moreover, fixation of the FMT 110 onto the incus is difficult in many cases with normal middle ear anatomy. During surgery, the short process of the incus ossicle is accessible without the need of complex surgical procedures. Among other things, the incus short process is more oval towards the main body and has a tapering round at the tip of the short process. This makes it difficult to crimp a clip of the FMT 110 onto the short process of the incus and the variations of the incus anatomy in the narrow facial recess. In addition, blood vessels within the incus need to be preserved to avoid necrosis of the incus.

WO2013/009807 from the inventor describes a transducer clamp comprising at the first end of the prosthesis member clamping fingers for securely engaging the outer surface of an enclosed mechanical signal transducer. An ossicle fastener at the second end of the prosthesis member is adapted for secure attachment to one ossicle of a patient middle ear. The ossicle fastener includes parallel planar fastener clips each having a clover shape with springy lobes surrounding an interior region defined by lobe connecting bends. This ossicle fastener is not suitable for coupling to the short process of the incus, because it is too bulky to fit into the middle ear cavity at the respective location and the clover shape with springy lobes cannot couple onto the conical outer surface of the short process of the incus, but slips off.

DE10204780B4 describes an ossicle fastener arrangement comprising two clamps for fixation of a magnet to the malleus ossicle. The clamps are separated from each other so as to fit the anatomy of the malleus and each clamp embraces the thin elongate, more cylindrically-shaped malleus bone. This fixation with conventional clamps is adapted for fixation to the malleus bone and therefore only suitable for fixation to the malleus ossicle. If this fixation were to be used for fixating to the incus, due to its anatomy, this fixation allows for fixating a floating mass transducer between the long and short process of the incus only. This area is surgically difficult to reach and in order for the surgeon to access the fixation location, the surgical procedure that needs to be carried out needs considerable invasive steps and bears the risk of damaging the facial nerve or the tendon on the short process of the incus. In addition, the exerted fixation force onto the incus ossicle for reliable fixation would potentially harm blood vessels within the incus ossicle. This is because the short and long process enclose an angle in between such that the clips of the ossicle fastener would apply opposing traction forces for fixation.

It is an object of the present invention to overcome these shortcomings of the prior art and provide a middle ear implant device and a middle ear coupling member for coupling an implantable mechanical signal transducer to the short process of the incus ossicle in the middle ear of a patient.

SUMMARY

Embodiments of the present invention are directed to a middle ear prosthesis coupling member comprising a transducer coupling element for coupling to a mechanical signal transducer, and an ossicle fastener coupled to the transducer coupling element and adapted for secure attachment to the short process of the incus ossicle of a patient middle ear. The ossicle fastener has parallel separated first and second fastener clips. Each fastener clip includes two opposing bendable legs adapted for forming an interior region for receiving the short process of the incus ossicle and an relieved opening between opposing leg ends displaceably providing access for the incus ossicle to the interior region. The fastener clips securely enclose the short process of the incus ossicle within the interior region. The first fastener clip is adapted for exerting a force to pull the ossicle fastener toward the short process of the incus ossicle. The second fastener clip is adapted for holding the ossicle fastener in place over lateral movement on the short process of the incus ossicle only and without substantially exerting a force to pull the ossicle fastener toward the short process of the incus ossicle. Vibration generated by the mechanical signal transducer is coupled by the prosthesis coupling member to the short process of the incus.

The first fastener clip may be adapted for coupling to the tip end of the short process of the incus. The second fastener clip may be adapted for coupling to the body end of the short process of the incus. The legs of the first fastener clip may be shorter than the legs of the second fastener clip. The middle ear prosthesis coupling member may further comprise a wing between the legs of the first fastener clip for secure gripping and fixation on the short process of the ossicle bone with a surgical tool. The legs of the fastener clips may have a rectangular or oval cross-section with the long side respectively long parallel to the semi-major axis side facing the outer surface of the short process of the incus ossicle. The two side-by-side opposing legs of the fastener clips may enclose an angle more than 0°. The angle may be 35°.

The opposing leg ends at the relieved opening may extend apart forming a guide for temporary pushing the opposing leg ends apart when clipping onto the incus ossicle. The transducer clamp and the ossicle fastener may be perpendicular to each other. The mechanical signal transducer may be directly fixed to the ossicle fastener. The coupling element may include a plurality of clamping fingers adapted for secure engagement to an outer surface of an enclosed mechanical signal transducer. The coupling element may include a mechanical vibration conducting elongate member for coupling vibration generated by the mechanical signal transducer to the prosthesis coupling member. The mechanical signal transducer may be separate from the prosthesis coupling member. The vibration conducting elongate member may be a rod with one end may be coupled to the prosthesis coupling member and the other end may be coupled to an outer surface of the mechanical signal transducer. The rod may be coupled with a hinge. The vibration conducting elongate member may be a liquid filled hose.

Further embodiments of the present invention are directed to a middle ear implant device comprising an external body worn audio processor and an implantable stimulator comprising a receiver and a mechanical signal transducer coupled to the short process of the incus ossicle including a middle ear prosthesis coupling member.

DETAILED DESCRIPTION

Various embodiments of the present invention are directed to a middle ear prosthesis coupling member to connect a mechanical signal transducer to an ossicle of a recipient patient, more specifically to the short process of the incus ossicle, thereby providing sound sensation to the patient. The mechanical signal transducer may be a floating mass transducer as known in the art and described for example in U.S. Pat. No. 5,913,815 (incorporated herein by reference). In a further embodiment the invention is directed to a middle ear implant device comprising a middle ear prosthesis coupling member.

Figure 2:
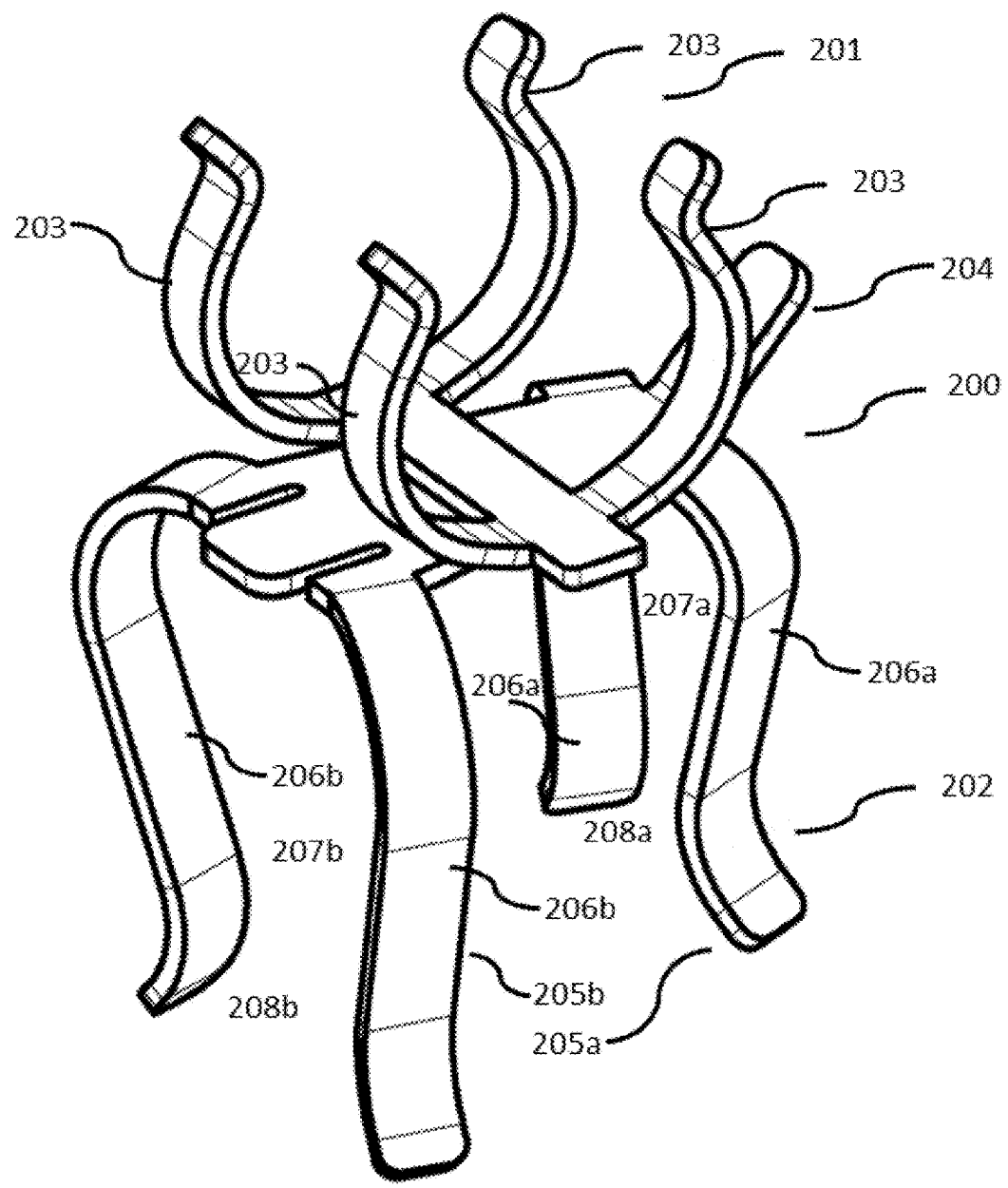
FIG. 2 shows an elevated perspective view of a middle ear prosthesis coupling member according to an embodiment of the present invention.

FIG. 2 shows an example of a middle ear prosthesis coupling member 200 according to an embodiment of the present invention. The middle ear prosthesis coupling member 200 comprising a transducer coupling element 201 and an ossicle fastener 202 coupled to the transducer coupling element 201 to couple mechanical vibrations from a mechanical signal transducer enclosed within the transducer coupling element 201 to the short process of the incus ossicle securely enclosed within the ossicle fastener 202. The transducer coupling element 201 may include multiple clamping fingers 203 for securely engaging the outer surface of an enclosed mechanical signal transducer, such as a floating mass transducer. The ossicle fastener 202 is adapted for secure attachment to the short process of the incus ossicle of a patient middle ear and comprising parallel separated first and second fastener clips 205a and 205b, respectively. Each fastener clip 205a and 205b comprising two opposing bendable legs 206a and 206b adapted for forming an interior region 207a and 207b for receiving the short process of the incus ossicle and an relieved opening 208a and 208b between opposing leg ends displaceably providing access for the incus ossicle to the interior region 207a and 207b, so that the fastener clips 205a and 205b securely enclose the short process of the incus ossicle within the interior region 207a and 207b. The legs 206a and 206b of the fastener clips 205a and 205b are flexible by use of an appropriate biocompatible material such as for example titanium alloy, superelastic nitinol or MP35.

Figure 1:
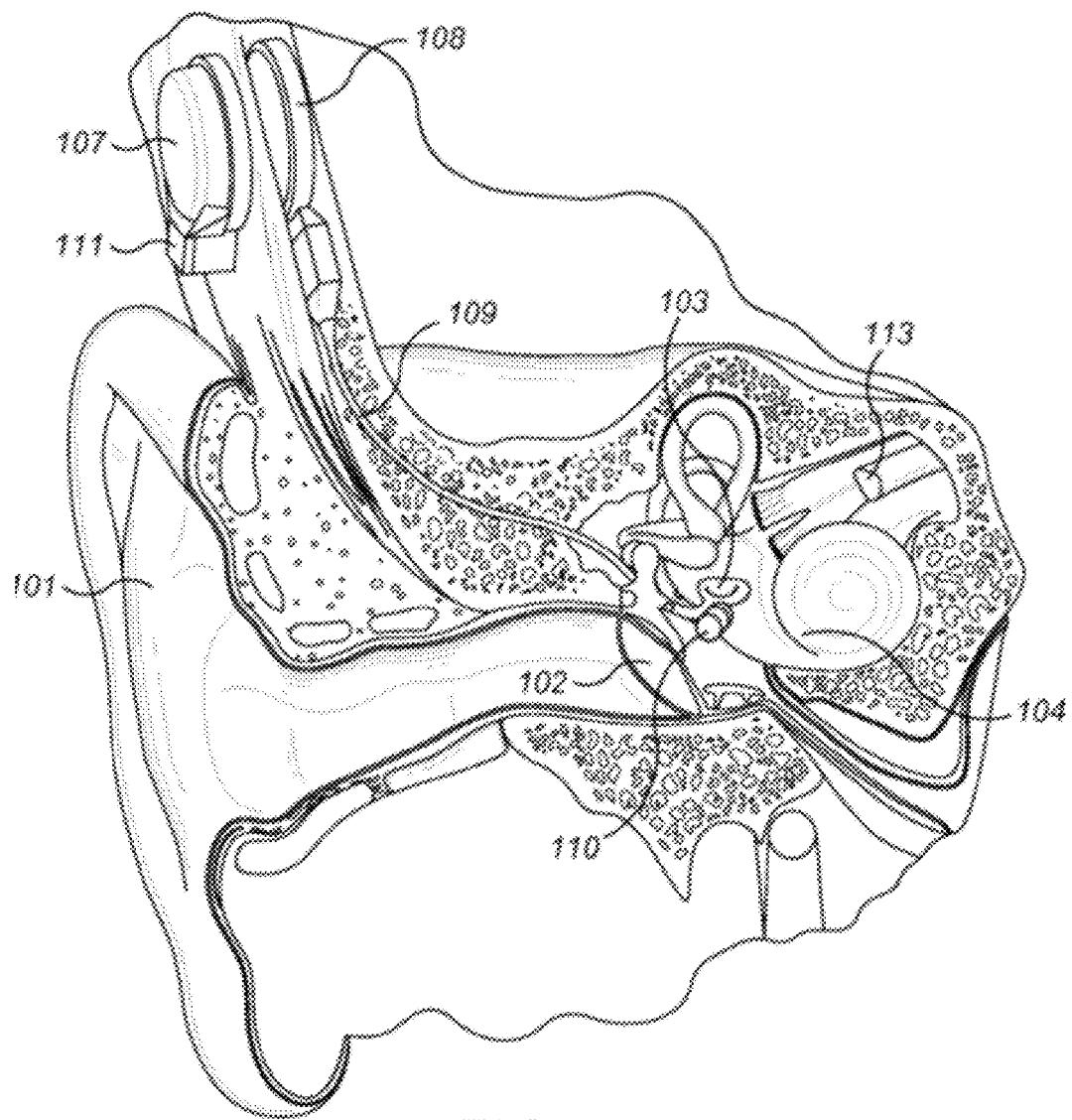
FIG. 1 shows various anatomical structures in a human ear containing a middle ear implant device.

In one embodiment of the present invention, the two opposing legs 206a and 206b of the fastener clips 205a and 205b may have a rectangular or oval cross section with the long side or semi-major axis snuggling the outer surface of the short process of the incus ossicle when fixated. This ensures a sufficiently large and flat seat-engaging surface and supports avoiding harm to the outer surface of the ossicle. This can for example be seen in FIG. 1 and FIG. 3 with the ossicle enclosed in the interior region for the exemplary rectangular cross section of the legs 206a and 206b. The rectangular legs may have in a further aspect of the invention rounded edges to avoid any damages by the edges to the outer surface of the ossicle when fixated and during fixation.

Figure 4:
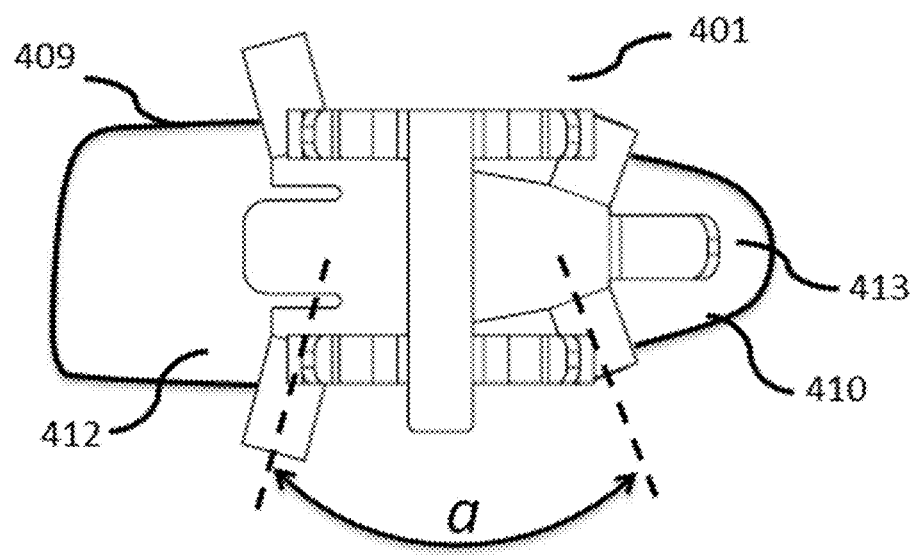
FIG. 4 shows a top front view of a middle ear prosthesis coupling member according to an embodiment of the present invention.

In a further embodiment the two side-by-side opposing legs of the fastener clips enclose an angle a of more than 0°, as shown in FIG. 4. The angle a is chosen in a way to reflect the various anatomies of the short process of the incus and ensures that the long respectively parallel to the semi-major axis side of the rectangular or oval legs are best snuggling the outer surface of the short process of the incus ossicle. It was found, that the angle a of 35° fulfills this criterion best. This is exemplary depicted in FIG. 4. The legs point of contact with the outer surface of the short process of the incus is with this angle a for most anatomies in the middle of the long respectively parallel to the semi-major axis side of the rectangular or oval legs.

Figure 3:
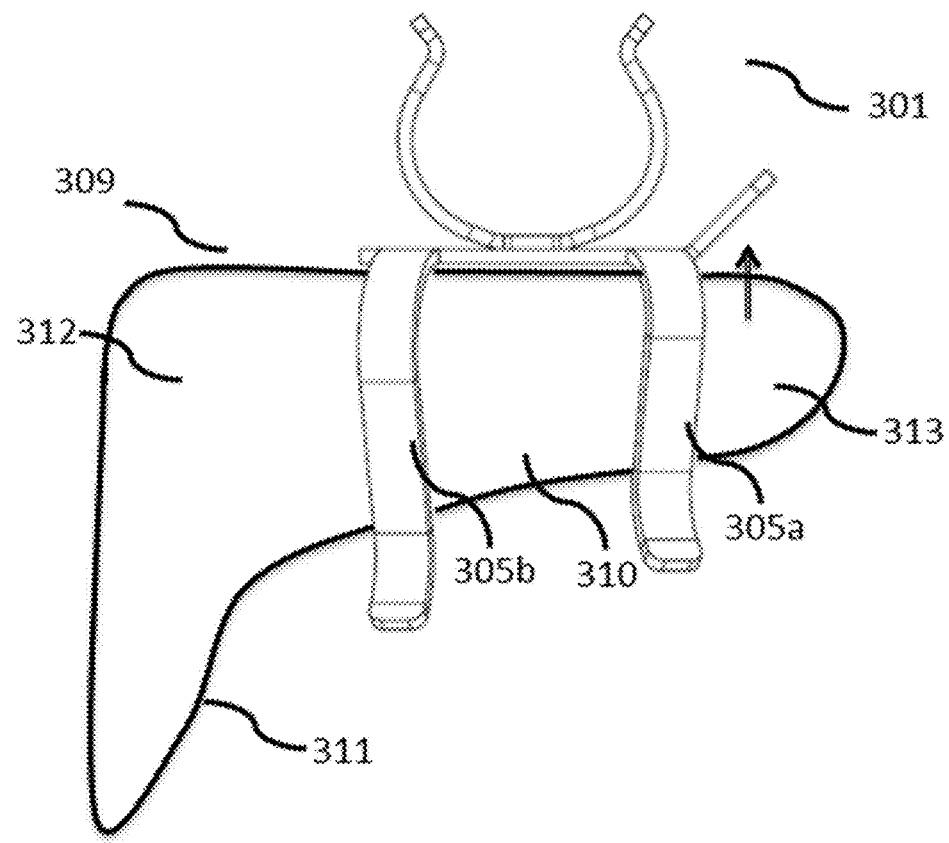
FIG. 3 shows a plan view of a middle ear prosthesis coupling member according to an embodiment of the present invention.

FIGS. 3 and 4 show the plan and front elevation view of a middle ear prosthesis coupling member 301 and 401 according one aspect of the present invention when fixated onto the short process 310 and 410 of the incus ossicle 309 and 409, respectively. The incus ossicle 309 and 409 consists of a main body 312 and 412, a short process 310 and 410 and a long process 311 (not visible in FIG. 4). It can be seen, that the short process has a conical shape, tapering from the main body 312 and 412 end toward the rounded tip end 313 and 413. The short process 310 and 410 cross-section varies over the different anatomies from the patients, but is in general more oval shaped. The first fastener clip 305a encloses the short process of the incus 310 and 410 at the tip end 313 and 413 and exerting a force to pull the ossicle fastener 301 and 401 toward the incus ossicle 309 and 409, thereby pushing the short process of the incus 310 and 410 into the interior region of the prosthesis coupling member and securely fixating the same within the interior region. In particular with reference to FIG. 3, the short process 310 of the incus ossicle 309 located in the interior region of the first fastener clip 305a is pushed upward by the two opposing bendable legs as shown with the arrow.

The invention is further described with reference to FIG. 3 in the following. Fixation of the middle ear prosthesis coupling member 301 with the first fastener clip 305a only does not prevent lateral movement. For example rotation of the prosthesis coupling member 301 about the first fastener clip 305a is easily possible. To prevent such lateral movement of the middle ear prosthesis coupling member 301 on the short process 310 of the incus ossicle 309, a second fastener clip 305b is attached to the body end of the short process 310 of the incus 309. The inventor has found, that in order for the prosthesis coupling member 301 to securely attach the short process 310 of the incus 309, the second fastener clip 305b has to be adapted for holding the ossicle fastener in place over lateral movement and without substantially exerting a force to pull the ossicle fastener toward the short process 310 of the incus 309. Moreover, the inventor has found that combining a fixation that exerts a force to pull the ossicle toward the middle ear prosthesis coupling member 301 and a fixation to prevent lateral movement is the only way to securely attach to the short process 310 of the incus 309 without the need of excessive fixation forces. Any other fixation alternatives known to the inventor require substantial surgical interventions with partial destruction of the ossicles; for example, by milling a recess into the ossicle, or fixation by means of a screw. The middle ear coupling member according to the present invention does not have these disadvantages.

The aforementioned combining of fixation according one embodiment of the invention may be achieved by adapting the first fastener clip 305a for coupling to the tip end of the short process 313 of the incus 309 and adapting the second fastener clip 305b for coupling to the body end of the short process 312 of the incus 309. In a further embodiment the legs of the first fastener clip 305a are shorter than the legs of the second fastener clip 305b. Choosing the length of the legs of the fastener clips that way achieves the fixation according one aspect of the invention of the middle ear prosthesis as set out further below in reference to FIGS. 5a and 5b.

Figure 5A:
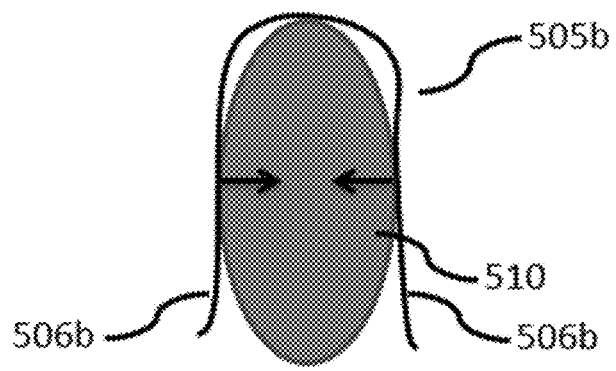
FIGS. 5a and 5b show cross-sectional views with the first and second fastener clips of the middle ear prosthesis coupling member snuggling the short process of the incus ossicle according to an embodiment of the present invention.
Figure 5B:
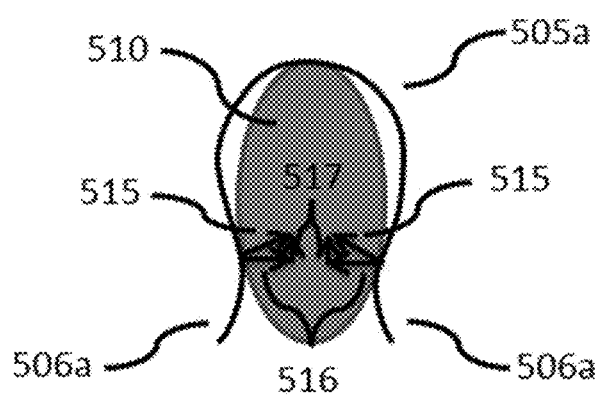

Reference is now made to FIGS. 5a and 5b. FIG. 5a shows a cross-sectional view of the second fastener clip 505b enclosing the short process of the incus 510 at the body end. The arrows show the applied forces from the two bendable opposing legs 506b when the short process of the incus 510 is enclosed in the interior region. It can be seen, that the force is mostly applied perpendicular to the relieved opening and without a lateral component to pull the fastener clip in relation to the incus ossicle 510 in any direction. Thus, only frictional forces hold the second fastener clip 505b in place and prevent the second fastener clip 505b from lateral movement. FIG. 5b shows the first fastener clip 505a enclosing the short process of the incus 510 at the tip end. The arrows show the applied forces 515 from the two bendable opposing legs 506a when the short process of the incus 510 is enclosed in the interior region. It can be seen, that the forces 515 split into two components. The component 516 for resetting the two opposing leg ends into the initial position when no ossicle is enclosed in the interior region. The component 515 is exerting the force to pull the fastener clip 505a toward the short process of the incus 510.

The prosthesis device 200 can be surgically installed via a conventional mastoidectomy/atticotomy approach through a very narrow posterior epitympanotomy as described, for example, by Mario Sanna and Hiroshi Sunose, "Middle Ear and Mastoid Microsurgery", 2012, Georg Thieme Verlag KG; incorporated herein by reference. With this surgical approach, the short process of the incus ossicle is directly accessible through the drilled hole and no need to complicate navigate within the middle ear cavity. The surgical tool may be straight, such as for example forceps. The surgeon only needs to grip the middle ear prosthesis coupling member 200 with the surgical tool at the wing 204, pass it straight on through the drilled hole and clip it on the short process of the incus ossicle.

In one embodiment the wing 204 is located between the legs of the first fastener clip 205a, so as to ease clipping and avoid turn away of the gripped ear prosthesis coupling member due to bending forces during clipping. In a further embodiment, the two opposing legs of the fastener clips 205a and 205b of the coupling member 200 may at the relieved opening 208a and 208b extend apart and forming a guide for temporary pushing the opposing leg ends apart when clipping onto the incuse ossicle. All this allows for a faster and safer surgical installation procedure. In addition, the geometry of the ossicle fastener 202 may be generically non-lateral so that there is no need for individual left- and right-side coupling members 200. There is therefore advantageously only one manufacturing process necessary and no extra shelves for left- and right-side coupling members 200 are needed.

Although various exemplary embodiments of the invention have been disclosed, it should be apparent to those skilled in the art that various changes and modifications can be made which will achieve some of the advantages of the invention without departing from the true scope of the invention.

What is claimed is:

1. A middle ear prosthesis coupling member comprising:
   a transducer coupling element adapted for coupling to a mechanical signal transducer; and
   an ossicle fastener coupled to the transducer coupling element and adapted for secure attachment to a short process of an incus ossicle of a patient middle ear, the ossicle fastener including parallel separated first and second fastener clips, each fastener clip having:
   i. two opposing bendable legs adapted to form an interior region for receiving the short process of the incus ossicle, and
   ii. a relieved opening between opposing leg ends displaceably providing access for the incus ossicle to the interior region, so that the fastener clips are adapted to securely enclose the short process of the incus ossicle within the interior region;
   wherein the first fastener clip is adapted for exerting a force to pull the ossicle fastener toward the short process of the incus ossicle; and
   wherein the second fastener clip is adapted for holding the ossicle fastener in place over lateral movement on the short process of the incus ossicle only and without substantially exerting a force to pull the ossicle fastener toward the short process of the incus ossicle;
   whereby the prosthesis coupling member is adapted to couple vibration generated by the mechanical signal transducer to the short process of the incus.

2. A middle ear prosthesis coupling member according to claim 1, wherein the first fastener clip is adapted for coupling to a tip end of the short process of the incus and the second fastener clip is adapted for coupling to a body end of the short process of the incus.

3. A middle ear prosthesis coupling member according to claim 2, wherein the legs of the first fastener clip are shorter than the legs of the second fastener clip.

4. A middle ear prosthesis coupling member according to claim 2, further comprising a wing between the legs of the first fastener clip for secure gripping and fixation on the short process of the ossicle bone with a surgical tool.

5. A middle ear prosthesis coupling member according to claim 1, wherein each leg has a rectangular cross-section with a long side adapted to face an outer surface of the short process of the incus ossicle.

6. A middle ear prosthesis coupling member according to claim 1, wherein each leg has an oval cross-section with a long diameter parallel to the semi-major axis side adapted to face an outer surface of the short process of the incus ossicle.

7. A middle ear prosthesis coupling member according to claim 6, wherein the two opposing bendable legs of each fastener clip encloses an angle more than 0°.

8. A middle ear prosthesis coupling member according to claim 7, wherein the angle is 35°.

9. A middle ear prosthesis coupling member according to claim 1, wherein leg ends of the opposing bendable legs at the relieved opening extend apart forming a guide for temporary pushing apart the leg ends when clipping onto the incus ossicle.

10. A middle ear prosthesis coupling member according to claim 1, wherein the transducer coupling element and the ossicle fastener are perpendicular to each other.

11. A middle ear prosthesis coupling member according to claim 1, wherein the mechanical signal transducer is directly fixated to the ossicle fastener.

12. A middle ear prosthesis coupling member according to claim 1, wherein the coupling element includes a plurality of clamping fingers adapted for secure engagement to an outer surface of an enclosed mechanical signal transducer.

13. A middle ear prosthesis coupling member according to claim 1, wherein the coupling element includes a mechanical vibration conducting elongate member for coupling vibration generated by the mechanical signal transducer to the prosthesis coupling member; the mechanical signal transducer being separate from the prosthesis coupling member.

14. A middle ear prosthesis coupling member according to claim 13, wherein the vibration conducting elongate member is a rod with one end coupled to the prosthesis coupling member and the other end coupled to an outer surface of the mechanical signal transducer.

15. A middle ear prosthesis coupling member according to claim 14, wherein the rod is coupled with a hinge.

16. A middle ear prosthesis coupling member according to claim 13, wherein the vibration conducting elongate member is a liquid filled hose.

17. A middle ear implant system including a prosthesis coupling member according to any of claims 1-16.

* * * * *